United States Patent
Hibst et al.

(10) Patent No.: US 6,797,839 B1
(45) Date of Patent: Sep. 28, 2004

(54) MULTI-METAL OXIDE MATERIALS WITH A TWO-PHASE STRUCTURE

(75) Inventors: Hartmut Hibst, Schriesheim (DE); Signe Unverricht, Mannheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/646,875

(22) PCT Filed: Mar. 26, 1999

(86) PCT No.: PCT/EP99/02081
§ 371 (c)(1),
(2), (4) Date: Oct. 5, 2000

(87) PCT Pub. No.: WO99/51341
PCT Pub. Date: Oct. 14, 1999

(30) Foreign Application Priority Data

Apr. 6, 1998 (DE) .......................... 198 15 278

(51) Int. Cl.$^7$ ...................... C07C 51/16; C07C 51/235; B01J 23/00; B01J 31/00; B01J 37/00
(52) U.S. Cl. ...................... 562/532; 562/534; 562/535; 502/104; 502/110; 502/113; 502/117; 502/255; 502/305; 502/306; 502/307; 502/308; 502/309; 502/310; 502/311; 502/312; 502/313; 502/314; 502/315; 502/316; 502/317; 502/318; 502/321; 502/322; 502/323; 502/335; 502/337
(58) Field of Search .......................... 502/104, 110, 502/113, 117, 255, 305–318, 321–323, 335, 337; 562/532, 534, 535

(56) References Cited

U.S. PATENT DOCUMENTS

| | | | | |
|---|---|---|---|---|
| 3,898,267 A | * | 8/1975 | Caporali et al. | 558/322 |
| 3,925,464 A | * | 12/1975 | Oda et al. | 562/535 |
| 3,939,208 A | * | 2/1976 | Cavaterra et al. | 568/479 |
| 4,031,135 A | * | 6/1977 | Engelbach et al. | 562/535 |
| 4,113,769 A | * | 9/1978 | Padovan et al. | 562/534 |
| 4,146,732 A | * | 3/1979 | Padovan et al. | 562/534 |
| 4,166,190 A | * | 8/1979 | White et al. | 562/534 |
| 4,223,161 A | * | 9/1980 | Shaw et al. | 562/534 |
| 4,259,211 A | * | 3/1981 | Krabetz et al. | 502/178 |
| 4,271,040 A | * | 6/1981 | Khoobiar | 502/211 |
| 4,289,654 A | * | 9/1981 | Bertolini et al. | 502/244 |
| 4,298,763 A | * | 11/1981 | Engelbach et al. | 568/479 |
| 4,318,738 A | * | 3/1982 | Masumoto et al. | 148/304 |
| 4,321,160 A | * | 3/1982 | Farrington et al. | 502/34 |
| 4,365,087 A | * | 12/1982 | Kadowaki et al. | 562/534 |
| 4,438,217 A | * | 3/1984 | Takata et al. | 502/205 |
| 4,471,061 A | * | 9/1984 | Shaw et al. | 502/34 |
| 4,528,398 A | * | 7/1985 | Callahan et al. | 562/534 |
| 4,537,874 A | * | 8/1985 | Sato et al. | 502/311 |
| 4,547,588 A | * | 10/1985 | Khoobiar | 562/535 |
| 4,656,157 A | * | 4/1987 | Hofmann et al. | 502/439 |
| 4,746,641 A | * | 5/1988 | Guttmann et al. | 502/202 |
| 4,985,592 A | * | 1/1991 | Ishii et al. | 562/534 |
| 5,364,825 A | * | 11/1994 | Neumann et al. | 502/311 |
| 5,449,821 A | * | 9/1995 | Neumann et al. | 562/546 |
| 5,493,052 A | * | 2/1996 | Tenten et al. | 562/534 |
| 5,583,084 A | * | 12/1996 | Martin et al. | 502/211 |
| 5,677,261 A | * | 10/1997 | Tenten et al. | 502/439 |
| 5,696,047 A | * | 12/1997 | Bremer et al. | 502/209 |
| 5,739,391 A | * | 4/1998 | Ruppel et al. | 562/532 |
| 5,807,531 A | * | 9/1998 | Hibst et al. | 252/518.1 |
| 5,910,608 A | * | 6/1999 | Tenten et al. | 562/532 |
| 5,959,143 A | * | 9/1999 | Sugi et al. | 562/534 |
| 6,084,126 A | * | 7/2000 | Hibst et al. | 562/535 |
| 6,124,499 A | * | 9/2000 | Hibst et al. | 562/535 |
| 6,184,173 B1 | * | 2/2001 | Hibst et al. | 502/300 |
| 6,429,332 B1 | * | 8/2002 | Tanimoto et al. | 562/532 |

FOREIGN PATENT DOCUMENTS

| | | |
|---|---|---|
| DE | 24 07 677 | 8/1975 |
| DE | 26 35 031 | 7/1977 |
| DE | 43 02 991 | 8/1994 |
| DE | 44 05 060 | 8/1995 |
| EP | 0 235 760 | 9/1987 |
| EP | 0 668 104 | 8/1995 |
| EP | 0 686 600 | 12/1995 |
| EP | 0 758 562 | 2/1997 |

* cited by examiner

Primary Examiner—Cam N. Nguyen

(57) ABSTRACT

Multimetal oxide materials containing molybdenum, vanadium, antimony, one or more of the elements W, Nb, Ta, Cr and Ce and nickel and, if required, one or more of the elements Cu, Zn, Co, Fe, Cd, Mn, Mg, Ca, Sr and Ba and having a 2-component structure are used for the gas-phase catalytic oxidative preparation of acrylic acid.

4 Claims, No Drawings

MULTI-METAL OXIDE MATERIALS WITH A TWO-PHASE STRUCTURE

The present invention relates to multimetal oxide materials of the formula I $$(A)_p(B)_q \quad (I),$$

where
A is $Mo_{12}V_aX^1_bX^2_cX^3_dX^4_eX^5_fX^6_gO_x$,
B is $X^7_1Sb_hH_iO_y$,
$X^1$ is W, Nb, Ta, Cr and/or Ce, preferably W, Nb and/or Cr,
$X^2$ is Cu, Ni, Co, Fe, Mn and/or Zn, preferably Cu, Ni, Co and/or Fe,
$X^3$ is Sb and/or Bi, preferably Sb,
$X^4$ is Li, Na, K, Rb, Cs and/or H, preferably Na and/or K,
$X^5$ is Mg, Ca, Sr and/or Ba, preferably Ca, Sr and/or Ba,
$X^6$ is Si, Al, Ti and/or Zr, preferably Si, Al and/or Ti,
$X^7$ is Ni and, if required, one or more of the elements selected from the group consisting of Cu, Zn, Co, Fe, Cd, Mn, Mg, Ca, Sr and Ba,
a is 1 to 8, preferably from 2 to 6,
b is 0.2 to 5, preferably from 0.5 to 2.5,
c is 0 to 23, preferably from 0 to 4,
d is 0 to 50, preferably from 0 to 3,
e is 0 to 2, preferably from 0 to 0.3,
f is 0 to 5, preferably from 0 to 2,
g is 0 to 50, preferably from 0 to 20,
h is 0.1 to 50, preferably from 0.2 to 20, particularly preferably from 0.2 to 5,
i is 0 to 50, preferably from 0 to 20, particularly preferably from 0 to 12,
x and y are each numbers which are determined by the valency and frequency of the elements in (I) other than oxygen and
p and q are each numbers which differ from zero and whose ratio p/q is from 20:1 to 1:80, preferably from 10:1 to 1:35, particularly preferably from 2:1 to 1:3,
which contain the moiety (A)p in the form of three-dimensional regions A having the chemical composition
A: $Mo_{12}V_aX^1_bX^2_cX^3_dX^4_eX^5_fX^6_gO_x$
and the moiety (B)q in the form of three-dimensional regions B having the chemical composition
B: $X^7_1Sb_hH_iO_y$,
the regions A, B being distributed relative to one another as in a mixture of finely divided A and finely divided B, with the proviso that, for the preparation of the multimetal oxide materials (I), at least one separately preformed oxometallate B, $$X^7_1Sb_hH_iO_y,$$

is present, which is obtainable by preparing a dry blend from suitable sources of the elemental constituents of the oxometallate B which contain at least a part of the antimony in oxidation stage +5 and calcining said dry blend at from 200 to <600° C., preferably from 200 to ≦580° C. particularly preferably from 250 to ≦550° C.

The present invention furthermore relates to processes for the preparation of multimetal oxide materials (I) and their use as catalysts for the gas-phase catalytic oxidation of acrolein to acrylic acid.

WO 96/27437 relates to multimetal oxide materials which contain the elements Mo, V, Cu and Sb as essential components and whose X-ray diffraction pattern has the line of strongest intensity at a 2θ value of 22.2°. WO 96/27437 recommends these multimetal oxide materials as suitable catalysts for the gas-phase catalytic oxidation of acrolein to acrylic acid. Furthermore, WO 96/27437 recommends using $Sb_2O_3$ as an antimony source for the preparation of these multimetal oxide materials. Prior preparation of an Sb-containing component is not disclosed in WO 96/27437.

EP-B 235760 relates to a process for the preparation of Sb, Mo, V and/or Nb-containing multimetal oxide materials which are suitable as catalysts for the gas-phase catalytic oxidation of acrolein to acrylic acid. EP-B 235760 recommends using an antimony prepared beforehand and calcined at from 600 to 900° C. as an antimony source for the preparation of these multimetal oxide materials.

The disadvantage of the multimetal oxide materials of the prior art is that, when they are used as catalysts for the gas-phase catalytic oxidation of acrolein to acrylic acid, their activity and the selectivity of the acrylic acid formation are not completely satisfactory.

It is an object of the present invention to provide novel multimetal oxide materials which, when used as catalysts for the gas-phase catalytic oxidation of acrolein to acrylic acid, have the disadvantages of the catalysts of the prior art to a reduced extent, if at all.

We have found that this object is achieved by the multimetal oxide materials (I) defined at the outset.

Very particularly preferred materials (I) are those whose regions A have a composition of the following formula (II)

$$Mo_{12}V_{a'}X^1_{b'}X^2_{c'}X^5_{f'}X^6_{g'}O_{x'}, \quad (II),$$

where
$X^1$ is W and/or Nb,
$X^2$ is Cu and/or Ni,
$X^5$ is Ca and/or Sr,
$X^6$ is Si and/or Al,
a' is from 2 to 6,
b' is from 0.5 to 2.5,
c' is from 0 to 4,
f' is from 0 to 2,
g' is from 0 to 2 and
x' is a number which is determined by the valency and frequency of the elements in (II) other than oxygen.

It is also advantageous if at least one of the moieties $(A)_p$, $(B)_q$ of the novel multimetal oxide materials (I) is contained in the latter in the form of three-dimensional regions having the chemical composition A or B, respectively, the maximum diameters $d_A$ and $d_B$, respectively, of which regions (longest connecting line between two points present on the surface (interface) of the region and passing through the center of gravity of the region) are from >0 to 300 μm, preferably from 0.01 to 100 μm, particularly preferably from 0.05 to 50 μm, very particularly preferably from 0.05 to 20 μm.

Of course, the maximum diameters can also be from 0.05 to 1.0 μm or from 75 to 125 μm (the experimental determination of the maximum diameters permits, for example, a microstructure analysis by means of a scanning electron microscope (SEM)).

As a rule, the moiety $(B)_q$ is present in the multimetal oxide materials according to the invention essentially in crystalline form, i.e. as a rule the regions B essentially comprise small crystallites whose maximum dimension is typically from 0.05 to 20 μm. However, the moiety $(B)_q$ can of course also be present in amorphous and/or crystalline form.

Particularly preferred multimetal oxide materials are those whose regions B essentially comprise crystallites which have the trirutile structure type of α- and/or β-copper antimonate $CuSb_2O_6$. α-$CuSb_2O_6$ crystallizes in a tetragonal trirutile structure (E. -O. Giere et al., J. Solid State Chem.

131 (1997) 263–274), whereas β-CuSb$_2$O$_6$ has a monoclinically distorted trirutile structure (A. Nakua et al., J. Solid State Chem. 91 (1991) 105–112 or reference diffraction pattern in index card 17-284 in the JCPDS-ICDD index 1989). Regions B which are also preferred are those which have the pyrochlore structure of the mineral partzite, a copper antimony copper hydroxide, having the variable composition Cu$_y$Sb$_{2-x}$(O, OH, H$_2$O)$_{6-7}$ (y≦2.0≦x≦1) (B. Mason et al., Mineral. Mag. 30 (1953) 100–112 or reference pattern in index card 7-303 of the JCPDS-ICDD index 1996).

Furthermore, the regions B may consist of crystallites which have the structure of copper antimonate Cu$_9$Sb$_4$O$_{19}$ (S. Shimada et al., Chem. Lett. 1983, 1875–1876 or S. Shimada et al., Thermochim. Acta 133 (1988) 73–77 or reference pattern in index card 45-54 of the JCPDS-ICDD index) and/or the structure of Cu$_4$SbO$_{4.5}$ (S. Shimada et al., Thermochim. Acta 56 (1982) 73–82 or S. Shimada et al., Thermochim. Acta 133 (1988) 73–77 or reference pattern in index card 36-1106 of the JCPDS-ICDD index).

Of course, the regions B may also consist of crystallites which are a mixture of the abovementioned structures.

The novel materials (I) are obtainable in a simple manner, for example by first separately preforming oxometallates B $$X^7{}_1Sb_hH_iO_y,$$

in finely divided form as starting material 1. The oxometallates B can be prepared by preparing a preferably intimate, advantageously finely divided dry blend from suitable sources of their elemental constituents and calcining said dry blend at from 200 to 1200° C., preferably from 200 to 850° C., particularly preferably from 250 to <600° C., frequently is ≦550° C. (as a rule for from 10 minutes to several hours). All that is essential to the invention is that at least a part of the oxometallates B of the starting material 1 (referred to below as oxometallates B*) is obtainable by preparing a preferably intimate, advantageously finely divided dry blend from suitable sources of the elemental constituents of the oxometallate B which contain at least a part of the antimony in oxidation state +5 and calcining said dry blend at from 200 to <600° C., preferably from 200 to ≦580° C., particularly preferably from 250 to ≦550° C., frequently ≦500° C. (as a rule for from 10 minutes to several hours). The calcination of the precursors of the oxometallates B can in general be carried out under inert gas or under a mixture of inert gas and oxygen, e.g. air, or under pure oxygen. Calcination under a reducing atmosphere is also possible. As a rule, the required calcination time decreases with increasing calcination temperature. Advantageously, the proportion of the oxometallates in the finely divided starting material 1 is at least 10, better at least 20, frequently at least 30 or at least 40, preferably at least 50, even better at least 60, particularly preferably at least 70 or at least 80, frequently at least 90 or 95, very particularly preferably 100, % by weight, based on the starting material 1.

Oxometallates B* are obtainable, for example, by the preparation methods described in detail in DE-A 24 076 77. Preferred among these is the procedure in which antimony trioxide and/or Sb$_2$O$_4$ are oxidized in an aqueous medium by means of hydrogen peroxide in an amount which is equal to or greater than the stoichiometric amount at from 40 to 100° C. to give antimony (V) oxide hydroxide hydrate, aqueous solutions and/or suspensions of suitable starting compounds of the other elemental constituents of the oxometallate B* are added before this oxidation, during this oxidation and/or after this oxidation, the resulting aqueous mixture is then dried (preferably spray-dried (inlet temperature: from 250 to 600° C., outlet temperature: from 80 to 130° C.)) and the intimate dry blend is then calcined as described.

In the process as described above, for example, aqueous hydrogen peroxide solutions having an H$_2$O$_2$ content of from 5 to 33 % by weight or more can be used. Subsequent addition of suitable starting compounds of the other elemental constituents of the oxometallate B* is advisable in particular when they are capable of catalytically decomposing the hydrogen peroxide. However, it will of course also be possible to isolate the resulting antimony (V) (V) oxide hydroxide hydrate from the aqueous medium and, for example, to dry blend it intimately with suitable finely divided starting compounds of the other elemental constituents of the oxometallate B* and then to calcine this intimate mixture as described.

It is important that the elemental sources of the oxometallates B, B* are either already oxides or are compounds that can be converted into oxides by heating in the presence or absence of oxygen.

In addition to the oxides, suitable starting compounds are therefore in particular halides, nitrates, formates, oxalates, acetates, carbonates and/or hydroxides (compounds such as NH$_4$OH, NH$_4$CHO$_2$, CH$_3$COOH, NH$_4$CH$_3$CO$_2$ or ammonium oxalate, which decompose and/or can be decomposed at the latest during calcination to give compounds escaping completely in gaseous form, may additionally be incorporated). In general, for the preparation of oxometallates B, the intimate mixing of the starting compounds can be carried out in dry or wet forms. If it is effected in dry form, the starting compounds are advantageously used in the form of finely divided powders. However, the intimate mixing is preferably carried out in wet form. Usually, the starting compounds are mixed with one another in the form of an aqueous solution and/or suspension. After the end of the mixing process, the fluid material is dried and is calcined after drying. The drying is preferably carried out by spray-drying.

After calcination is complete, the oxometallates B, B* may be comminuted again (for example by wet or dry milling, for example in a ball mill or by jet milling) and the particle class having a maximum particle diameter (as a rule >0 to 300 μm, usually from 0.01 to 200 μm, preferably from 0.01 to 100 μm, very particularly preferably from 0.05 to 20 μm) which is in the maximum diameter range desired for the novel multimetal oxides (I) is separated off from the resulting powder, usually comprising essentially the spherical particles by classification to be carried out in a manner known per se (for example wet or dry sieving).

The preferred method of preparation for oxometallates B* of the formula (X$^7{}_1$)Sb$_h$H$_i$O$_y$, where X$^7$ is Ni or may be Cu and/or Zn, comprises first converting antimony trioxide and/or Sb$_2$O$_4$ in an aqueous medium by means of hydrogen peroxide into a preferably finely divided Sb(V) compound, e.g. antimony (V) oxide hydroxide hydrate, adding an ammoniacal aqueous solution of nickel carbonate and, if required, zinc carbonate and/or copper carbonate (which may have, for example, the composition Cu$_2$(OH)$_2$CO$_3$) to the resulting aqueous suspension, drying the resulting aqueous mixture, for example spray-drying said mixture as described, and calcining the resulting powder in the manner described, if required after subsequent kneading with water and subsequent extrusion and drying.

In the case of oxometallates B differing from oxometallates B*, it proves particularly advantageous to start from an aqueous antimony trioxide suspension and to dissolve the X$^7$ elements as nitrate and/or acetate therein, to spray-dry the resulting aqueous mixture as described and then to calcine the resulting powder as described.

According to the invention, the proportion of Ni in X$^7$ may be ≧1 or ≧5 or ≧10 or ≧20 or ≧30 or ≧40 or ≧50, mol %. Of course, the abovementioned proportion of Ni may also be ≧60 or ≧70 or ≧80 or ≧90, mol %. However, X$^7$ may also consist of Ni alone.

In the preparation of multimetal oxide materials (I), the starting materials 1 preformed as described can then be brought into intimate contact with suitable sources of the elemental constituents of the multimetal oxide material A, $$Mo_{12}V_aX^1_bX^2_cX^3_dX^4_eX^5_fX^6_gO_x,$$

in the desired ratio and a resulting dry blend can be calcined at from 250 to 500° C., it being possible to carry out the calcination under inert gas (e.g. $N_2$), a mixture of inert gas and oxygen (e.g. air), reducing gases, such as hydrocarbons (e.g. methane), aldehydes (e.g. acrolein), or ammonia, or under a mixture of $O_2$ and reducing gases (e.g. all the abovementioned ones), as described, for example, in DE-A 43 359 73. In the case of a calcination under reducing conditions, it should be ensured that the metallic constituents are not reduced to the elements. The calcination time is as a rule a few hours and usually decreases with increasing calcination temperatures. As is generally known, all that is important with regard to the sources of the elemental constituents of the multimetal oxide material A is that they are either already oxides or compounds which can be converted into oxides by heating, at least in the presence of oxygen. In addition to the oxides, suitable starting compounds are in particular halides, nitrates, formates, oxalates, citrates, acetates, carbonates or hydroxides. Suitable starting compounds of Mo, V, W and Nb are also their oxo compounds (molybdates, vanadates, tungstates and niobates) or the acids derived from these.

The starting material 1 can be brought into intimate contact with the sources of the multimetal oxide material A (starting material 2) either in dry form or in wet form. In the latter case, it is merely necessary to ensure that the preformed multimetal oxides B, B* do not go into solution. In an aqueous medium, the latter is usually ensured at a pH which does not deviate too greatly from 7 and at ≦60° C. or ≦40° C., respectively. If said substances are brought into contact in wet form, drying is usually subsequently carried out to give a dry material (preferably by spray-drying). Such a dry material is automatically obtained in the course of dry blending.

Examples of possible mixing methods are therefore:
a. mixing a dry, finely divided, preformed starting material 1 with dry, finely divided starting compounds of the elemental constituents of the desired multimetal oxide A in the desired ratio in a mixer, kneader or mill;
b. preforming a finely divided multimetal oxide A by intimate mixing of suitable starting compounds or its elemental constituents (dry or wet) and then calcining the resulting intimate dry blend at from 250 to 500° C. (with regard to the calcination time, calcination atmosphere and elemental sources, the statements made above are applicable); converting the preformed multimetal oxide A into finely divided form and mixing it with the finely divided starting material 1 in the desired ratio as in a.; in this method of mixing, final calcination of the resulting mixture is not essential;
c. stirring the required amount of preformed starting material 1 into an aqueous solution and/or suspension of starting compounds of the elemental constituents of the desired multimetal oxide A and then carrying out spray-drying; instead of the starting compounds of the elemental constituents of the desired multimetal oxide A, it is of course also possible to use a multimetal oxide A itself, already preformed according to b.

All mixing methods between a., b. and/or c. can of course also be used. The resulting intimate dry blend can then be calcined as described and then shaped to give the desired catalyst geometry, or vice versa. In principle, the calcined dry blend (or optionally uncalcined dry blend when mixing method b. is used) can however also be used in the form of a powder catalyst.

Our own investigations have shown that, on calcination of the dry blend comprising the starting material 1 and starting material 2, essentially no fusion of the constituents of the starting material 1 with those of the starting material 2 take place and the structure type or the crystallites contained in the starting material 1 is frequently essentially retained as such.

As indicated above, this opens up the possibility, after milling of the preformed starting mixture 1, of separating off the particle class having the maximum particle diameter (as a rule from >0 to 300 μm, preferably from 0.01 to 100 μm, particularly preferably from 0.05 to 20 μm) which is in the maximum diameter range desired for the multimetal oxide material (I) from the resulting powder frequently essentially comprising spherical particles by classification to be carried out in a manner known per se (for example wet or dry sieving) and thus using said particle class in a tailor-made manner for the preparation of the desired multimetal oxide material.

When the novel multimetal oxide materials (I) are used as catalysts for the gas-phase catalytic oxidation of acrolein to acrylic acid, the shaping to give the desired catalyst geometry is preferably carried out by application to premolded inert catalyst supports, it being possible to effect application before or after the final calcination. It is possible to use the usual support materials, such as porous or nonporous aluminas, silica, thorium dioxide, zirconium dioxide, silicon carbide or silicates, such as magnesium silicate or aluminum silicate. The supports may have a regular or irregular shape, regularly shaped supports having a pronounced surface roughness, for example spheres or hollow cylinders, being preferred. Among these in turn, spheres are particularly advantageous. The use of essentially nonporous spherical steatite supports which have a rough surface and whose diameter is from 1 to 8 mm, preferably 4 to 5 mm, is particularly advantageous. The coat thickness of the active material is advantageously chosen to be in the range from 50 to 500 μm, preferably from 150 to 250 μm. It should be pointed out here that, for coating the supports in the preparation of such coated catalysts, the powder material to be applied is as a rule moistened and is dried again after the application, for example by means of hot air.

For the preparation of the coated catalysts, the supports are as a rule coated in a suitable rotatable container, as previously disclosed, for example, in DE-A 2909671 or EP-A 293859. As a rule, the relevant material is calcined before coating of the supports.

The coating and calcination process according to EP-A 293 859 can be used in a suitable manner known per se so that the resulting multimetal oxide active materials have a specific surface area of from 0.50 to 150 m$^2$/g, a specific pore volume of from 0.10 to 0.90 cm$^3$/g and a pore diameter distribution such that at least 10% of the total pore volume are accounted for in each case by the diameter ranges from 0.1 to <1 μm, from 1.0 to <10 μm and 10 μm to 100 μm. The pore diameter distributions stated as being preferred in EP-A 293 859 may also be established.

Of course, the novel multimetal oxide materials may also be operated as unsupported catalysts. In this respect, the intimate dry blend comprising the starting materials 1 and 2 is preferably compacted directly to give the desired catalyst geometry (for example by means of pelleting or extrusion) it being possible, if required, to add conventional assistants, e.g. graphite or stearic acid, as lubricants and/or molding assistants and reinforcing materials such as microfibers of glass, asbestos, silicon carbide or potassium titanate, and is calcined. Here too, calcination can generally be effected prior to the shaping procedure. Preferred geometries for unsupported catalysts are hollow cylinders having an external diameter and a length of 2 to 10 mm and a wall thickness of 1 to 3 mm.

The novel multimetal oxide materials are especially suitable as catalysts having high activity and selectivity (at a given conversion) for the gas-phase catalytic oxidation of acrolein to acrylic acid. The process is usually carried out using acrolein which was produced by the catalytic gas-phase oxidation of propene. As a rule, the acrolein-containing reaction gases from this propene oxidation are used without intermediate purification. Usually, the gas-phase catalytic oxidation of acrolein is carried out in tube-bundle reactors as a heterogeneous fixed-bed oxidation. Oxygen, advantageously diluted with inert gases (for example in the form of air), is used as an oxidizing agent in a manner known per se. Suitable diluent gases are, for example, $N_2$, $CO_2$, hydrocarbon, recycled reaction gases and/or steam. As a rule, an acrolein:oxygen:steam inert gas volume ratio of 1:(1 to 3):(0 to 20):(3 to 30), preferably 1:(1 to 3):(0.5 to 10):(7 to 18), is established in the acrolein oxidation. The reaction pressure is in general from 1 to 3 bar and the total space velocity is preferably from 1000 to 3500 l (s.t.p.)/l/h. Typical multitube fixed-bed reactors are described, for example, in DE-A 2830765, DE-A 2 201 528 or U.S. Pat. No. 3,147,084. The reaction temperature is usually chosen so that the acrolein conversion in a single pass is above 90%, preferably above 98%. Usually, reaction temperatures of from 230 to 330° C. are required for this.

In addition to the gas-phase catalytic oxidation of acrolein to acrylic acid, the novel products are, however, also capable of catalyzing the gas-phase catalytic oxidation of other organic compounds, in particular other alkanes, alkanols, alkanals, alkenes and alkenols, preferably of 3 to 6 carbon atoms (e.g. propylene, methacrolein, tert-butanol, methyl ether of tert-butanol, isobutene, isobutane or isobutyraldehyde), to give olefinically unsaturated aldehydes and/or carboxylic acids, and the corresponding nitriles (ammoxidation, especially of propene to acrylonitrile and of isobutene or tert-butanol to methacrylonitrile). The preparation of acrolein, methacrolein and methacrylic acid may be mentioned by way of example. However, they are also suitable for the oxidative dehydrogenation of olefinic compounds.

Unless stated otherwise, the conversion, selectivity and residence time are defined as follows in this publication:

$$\text{Conversion } C \text{ to acrolein}(\%) = \frac{\text{Number of moles of acrolein converted}}{\text{Number of moles of acrolein used}} \times 100;$$

$$\text{Selectivity } S \text{ of the acrylic acid formation } \% = \frac{\text{Number of moles of acrolein converted into acrylic acid}}{\text{Total number of moles of acrolein converted}} \times 100;$$

$$\text{Residence time (sec)} = \frac{\text{Empty reactor volume filled with catalyst (l)}}{\text{Sythesis gas throughput}} \times 3600.$$
$$(l(STP)/h)$$

EXAMPLES

I. Catalyst Preparation

Example a) Preparation of the starting material 1 946.0 g of $Sb_2O_3$ having an Sb content of 83.0% by weight were suspended in 4 l of water while stirring. 822.4 g of a 30% strength by weight aqueous $H_2O_2$ solution were added at room temperature (25° C.). The suspension was then heated to 100° C. in the course of 1 hour with further stirring and was refluxed at this temperature for 5 hours. A solution of 536.0 g of $Cu(CH_3COO)_2.H_2O$ having a Cu content of 32.0% by weight and 74.6 g of $Ni(CH_3COO)_2.4H_2O$ having an Ni content of 23.6% by weight in 4 l of water was then added to the aqueous suspension at 100° C. in the course of 30 minutes, the temperature of the total aqueous mixture decreasing to 60° C. At this temperature, 407.9 g of a 25% strength by weight aqueous ammonia solution were then added. Thereafter, the aqueous suspension was stirred for a further 2 hours at 80° C. and then cooled to room temperature (25° C.). Finally, the aqueous suspension was spray-dried (inlet temperature: 350° C., outlet temperature: 110° C.). The resulting spray-dried powder was heated stepwise in a rotary oven (2 l internal volume) with passage of 100 l (s.t.p.)/h of air, initially to 150° C. in the course of 1 hour, then to 200° C. in the course of 4 hours and finally to 300° C. in the course of 2 hours, and was kept at the last-mentioned temperature for 1 hour. Thereafter, the powder obtained was heated to 400° C. in the course of 1.5 hours and was thermostatted at this temperature for 1 hour. The powder obtained had a specific BET surface area (determined according to DIN 66131, by gas adsorption ($N_2$) according to Brunauer-Emmet-Teller) of 48.0 $m^2/g$ and the stoichiometry $(Cu_{0.9}Ni_{0.1})Sb_{2.15}O_y$ ($y \leq 6.375$). The powder exhibited the X-ray diffraction reflections of the mineral partzite and thus corresponded to reference spectrum 7-0303 of the JCPDS-ICDD index 1996.

b) Preparation of the starting material 2 682.4 g of ammonium heptamolybdate tetrahydrate (81.5% by weight of $MoO_3$), 131.0 g of ammonium metavanadate (77.3% by weight of $V_2O_5$) and 114.6 g of ammonium paratungstate heptahydrate (89.0 % by weight of $WO_3$) were dissolved in succession in 5030 g of water at 95° C. The aqueous solution (starting material 2) was thus based on the following stoichiometry:

$$Mo_{3.86}V_{1.11}W_{0.44} = (Mo_{12}V_{3.45}W_{1.37})_{0.32}.$$

c) Preparation of a multimetal oxide material M and of a coated catalyst CC

The clear, orange-colored solution (starting material 2) obtained above was cooled to 25° C. and 150.0 g of ammonium acetate were added. 239.0 g of the starting material 1 were stirred into the aqueous solution cooled to 25° C. so that the molar ratio of the abovementioned stoichiometric units was 0.56 (starting material 1) to 0.32 (starting material 2). The resulting suspension was stirred for 1 hour at 25° C. and the aqueous mixture was then spray-dried. The spray-dried powder was then kneaded with a mixture of 70% by weight of water and 30% by weight of acetic acid (0.35 kg of liquid/kg of spray-dried powder) (LUK 2.5 kneader from Werner and Pfleiderer). The kneaded material obtained was dried for 16 hours at 110° C. in a through-circulation oven through which air flowed. The subsequently comminuted kneaded material was calcined in a cylindrical rotary oven (internal diameter: 12.5 cm, heated length: 50 cm) through which an air/nitrogen mixture (15 l (s.t.p./h of air and 200 l (s.t.p.)/h of nitrogen) flowed. 700 g of material to be calcined were introduced into the heated zone of the rotary oven. In the course of the calcination, heating was initially carried out to 325° C. in the course of 60 minutes and this temperature was then maintained for 4 hours. Thereafter, heating was carried out to 400° C. in the course of 20 minutes and this temperature was maintained for 1 hour. The resulting catalytically active multimetal oxide material had the following gross stoichiometry:

$$Mo_{3.86}V_{1.11}W_{0.44}Cu_{0.50}Ni_{0.56}Sb_{1.20}O_x = (Mo_{12}V_{3.45}W_{1.37})_{0.32}$$
$$((Cu_{0.9}Ni_{0.1})Sb_{2.15}O_y)_{0.56}.$$

After milling of the calcined active material, nonporous steatite spheres having a rough surface and a diameter of from 4 to 5 mm were coated with said active material in a rotating drum, in an amount of 60 g of active powder per 400 g of steatite spheres, with simultaneous addition of water (coating process according to DE-A 4 442 346). The resulting coated catalyst CC was then dried with air at 110° C.

Comparative Example

The preparation of a comparative multimetal oxide material CM and of a comparative coated catalyst CCC was carried out as in the example, except that, in the calcination to prepare the active material 1, heating was carried out finally not for 1 hour at 400° C., but for 1 hour at 800° C.

II. Use of the Coated Catalysts from I. as Catalysts for the Gas-phase Oxidation of Acrolein to Acrylic Acid The coated catalysts were introduced into a tubular reactor (V2A stainless steel, 25 mm internal diameter, 2000 g catalyst bed, thermostatted by means of a salt bath) and loaded with a gaseous mixture having the composition
5% by volume of acrolein,
7% by volume of oxygen,
10% by volume of steam and
78% by volume of nitrogen
using a residence time of 2.0 seconds.

The salt bath temperature was always adjusted so that, after forming was complete, a standard acrolein conversion C of 99% resulted after a single pass. The product gas mixture flowing out of the reactor was analyzed by gas chromatography. The results for the selectivity of the acrylic acid formation using the various catalysts and the required salt bath temperatures are shown in the table below:

| Catalyst | Salt bath temperature (° C.) | S % |
|---|---|---|
| CC | 266 | 95.5 |
| CCC | 276 | 93.2 |

We claim:

1. A multimetal oxide material of the formula I $$(A)_p(B)_q \quad (I),$$

where
A is $Mo_{12}V_aX^1_bX^2_cX^3_dX^4_eX^5_fX^6_gO_x$,
B is $X^7_1Sb_hH_iO_y$,
$X^1$ is W, Nb, Ta, Cr and/or Ce,
$X^2$ is Cu, Ni, Co, Fe, Mn and/or Zn,
$X^3$ is Sb and/or Bi,
$X^4$ is Li, Na, K, Rb, Cs and/or H,
$X^5$ is Mg, Ca, Sr and/or Ba,
$X^6$ is Si, Al, Ti and/or Zr,
$X^7$ is Ni and, optionally, one or more elements selected from the group consisting of Cu, Zn, Co, Fe, Cd, Mn, Mg, Ca, Sr and Ba,
a is 1 to 8,
b is 0.2 to 5,
c is 0 to 23,
d is 0 to 50,
e is 0 to 2,
f is 0 to 5,
g is 0 to 50,
h is 0.1 to 50,
i is 0 to 50,
x and y are each numbers which are determined by the valency and frequency of the elements in (I) other than oxygen and
p and q are each numbers which differ from zero and whose ratio p/q is from 20:1 to 1:80,
which contains the moiety $(A)_p$ in the form of three-dimensional regions A having the chemical composition
A: $Mo_{12}V_aX^1_bX^2_cX^3_dX^4_eX^5_fX^6_gO_x$
and the moiety $(B)_q$ in the form of three-dimensional regions B having the chemical composition
B: $X^7_1Sb_hH_iO_y$,
the regions A and B are distributed relative to one another as in a mixture of finely divided A and finely divided B,
with the proviso that, for the preparation of the multimetal oxide materials (I), at least one separately preformed oxometallate B, $$X^7_1Sb_hH_iO_y,$$

is present, which is obtained by preparing a dry blend from sources of the elemental constituents of the oxometallate B which contain at least a part of the antimony in oxidation state +5, and calcining said dry blend at a temperature of from 200 to below 600° C.

2. A process for preparation of a multimetal oxide as claimed in claim 1, wherein an oxometallate B, $$X^7_1Sb_hH_iO_y,$$

is preformed in finely divided form and then mixed with sources of the elemental constituents of a multimetal oxide material A, $$Mo_{12}V_aX^1_bX^2_cX^3_dX^4_eX^5_fX^6_gO_x,$$

in the desired ratio to result in a dry blend, and is subsequently calcined at a temperature from 250 to 500° C., wherein at least a portion of the oxometallate B is obtained by preparing a dry blend from sources of the elemental constituents of the oxometallate B which contain at least a part of the antimony in oxidation state +5, and calcining said dry blend at a temperature from 200 to below 600° C.

3. A process for a gas-phase catalytic oxidative preparation of acrylic acid from acrolein, comprising oxidizing acrolein in the presence of a catalyst, and wherein the catalyst comprises a multimetal oxide as claimed in claim 1.

4. A process for preparation of an oxometallate B of the formula $$X^7_1Sb_hH_iO_y,$$

where
$X^7$ is Ni and, optionally, one or more elements selected from the group consisting of Cu and Zn,
h is 0.1 to 50,
i is 0 to 50 and
y is a number which is determined by the valency and frequency of the elements in the formula other than oxygen,
wherein antimony trioxide or $Sb_2O_4$ is oxidized in an aqueous medium by means of hydrogen peroxide initially to give an Sb(V) compound, an aninomical aqueous solution of nickel carbonate and, optionally, a zinc carbonate or, copper carbonate is added to the aqueous medium to obtain a mixture and the mixture obtained is dried and calcined at a temperature of 200 to below 600° C.

* * * * *